(12) United States Patent
Laricchia

(10) Patent No.: US 9,126,879 B2
(45) Date of Patent: Sep. 8, 2015

(54) PROCESS FOR TREATING A HYDROCARBON STREAM AND AN APPARATUS RELATING THERETO

(71) Applicant: UOP, LLC, Des Plaines, IL (US)

(72) Inventor: Luigi Laricchia, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 193 days.

(21) Appl. No.: 13/920,432

(22) Filed: Jun. 18, 2013

(65) Prior Publication Data

US 2014/0371505 A1 Dec. 18, 2014

(51) Int. Cl.
*C07C 7/144* (2006.01)
*C07C 7/11* (2006.01)
*C10G 70/00* (2006.01)

(52) U.S. Cl.
CPC . *C07C 7/144* (2013.01); *C07C 7/11* (2013.01); *C10G 70/00* (2013.01)

(58) Field of Classification Search
None
See application file for complete search history.

(56) References Cited

U.S. PATENT DOCUMENTS

| | | | |
|---|---|---|---|
| 2,230,654 A | 2/1941 | Plunkett | |
| 2,594,311 A | 4/1952 | Johnson et al. | |
| 2,726,992 A | 12/1955 | Easthagen et al. | |
| 4,199,440 A | 4/1980 | Verachtert | |
| 4,208,541 A | 6/1980 | McClure | |
| 4,336,233 A | 6/1982 | Appl et al. | |
| 4,461,749 A | 7/1984 | Thorn | |
| 4,490,246 A | 12/1984 | Verachtert | |
| 4,562,300 A | 12/1985 | LaFoy | |
| 4,626,341 A | 12/1986 | Verachtert | |
| 4,666,689 A | 5/1987 | Maple et al. | |
| 4,735,704 A | 4/1988 | Kister et al. | |
| 4,808,765 A | 2/1989 | Pearce et al. | |
| 4,957,715 A | 9/1990 | Grover et al. | |
| 5,149,340 A | 9/1992 | Waycuilis | |
| 5,246,619 A | 9/1993 | Niswander | |
| 5,456,661 A | 10/1995 | Narciso, Jr. | |
| 5,601,702 A | 2/1997 | Yan | |
| 5,877,386 A | 3/1999 | Schubert | |
| 5,997,731 A | 12/1999 | Suarez | |
| 6,071,484 A * | 6/2000 | Dingman et al. | 423/229 |
| 6,334,949 B1 | 1/2002 | Bruno et al. | |
| 6,852,144 B1 | 2/2005 | Wagner et al. | |
| 7,119,244 B2 | 10/2006 | Smith, Jr. | |
| 7,223,332 B1 | 5/2007 | Tertel | |
| 7,326,333 B2 | 2/2008 | Laricchia et al. | |

(Continued)

FOREIGN PATENT DOCUMENTS

| | | |
|---|---|---|
| EP | 0227259 A1 | 7/1987 |
| GB | 815193 | 6/1959 |
| WO | 2005121279 | 12/2005 |

OTHER PUBLICATIONS

"New Developments . . . Coalescers Eliminate Gasoline Haze", Hydrocarbon Processing, Feb. 2001, vol. 80, No. 2, pp. 118, 124.

(Continued)

*Primary Examiner* — Tam M Nguyen
(74) *Attorney, Agent, or Firm* — James C. Paschall

(57) ABSTRACT

One exemplary embodiment can be a process for treating a hydrocarbon stream. The stream can include passing the hydrocarbon stream into a vessel containing a packed zone and a coalescing zone, passing an amine stream into the vessel at a location above an inlet for the hydrocarbon stream, and withdrawing the hydrocarbon stream.

19 Claims, 3 Drawing Sheets

(56) References Cited

U.S. PATENT DOCUMENTS

| | | | |
|---|---|---|---|
| 7,381,309 | B1 | 6/2008 | Laricchia et al. |
| 7,604,724 | B2 | 10/2009 | Mortson |
| 7,875,185 | B2 | 1/2011 | Zhang |
| 8,028,975 | B2 | 10/2011 | Tertel et al. |
| 8,080,087 | B2 | 12/2011 | Falkiner et al. |
| 8,088,281 | B2 | 1/2012 | Falkiner et al. |
| 8,173,856 | B2 | 5/2012 | Tertel |
| 8,308,957 | B2 | 11/2012 | Zhang et al. |
| 8,313,718 | B2 | 11/2012 | Bedell |
| 2009/0134068 | A1 | 5/2009 | Falkiner et al. |
| 2009/0151237 | A1 | 6/2009 | Takegoshi et al. |
| 2011/0142738 | A1 | 6/2011 | Pandya et al. |
| 2012/0000827 | A1 | 1/2012 | Krupa et al. |
| 2014/0091010 | A1* | 4/2014 | Banerjee et al. ............... 208/236 |
| 2014/0371508 | A1* | 12/2014 | Laricchia et al. ............. 585/802 |
| 2014/0371509 | A1* | 12/2014 | Laricchia et al. ............. 585/818 |
| 2015/0005562 | A1* | 1/2015 | Tertel et al. .................. 585/802 |

OTHER PUBLICATIONS

Doran et al., "Removal of Trace H2S and COS from Liquid Streams", Petroleum Technology Quarterly, Autumn 1996, pp. 41-44.

Pai et al., "Gas Processing Options for Mercaptans and Carbonyl Sulfide Removal from NG and NGL Streams", AIChE 1993 Spring National Meeting Presentation paper, Mar. 28, 1993, No. Preprint N. 75g, p. 25 pages.

McClure et al., "Amine Process Removes COS from Propane Economically", The Oil and Gas Journal, Jul. 2, 1979, vol. 77, No. 27, pp. 106-108.

Nielsen et al., "Treat LPGs with Amines", Hydrocarbon Processing, Sep. 1997, vol. 76, No. 9, pp. 49-50, 53-54, 56, 58-59.

"Coalescer Removes Dispersed, Nondissolved Liquid Contaminants", Chemical Engineering Progress, Apr. 2001, vol. 97, No. 4, p. 27.

Weber et al., "The Cosden/Malaprop Process for Light Hydrocarbon Desulfurization", National Petroleum Refiners Association 1981 NPRA Annual Meeting Presentation, Mar. 29-31, 1981, No. PAP.N. AM-81-49, p. 14 pages.

Wines et al., "Difficult Liquid—High-Performance, Polymer-Fiber Coalescers Break Up Hard-to-Handle Emulsions and Dispersions", Chemical Engineering, vol. 104, No. 12, Dec. 1997, pp. 104-109.

U.S. Appl. No. 13/920,407, filed Jun. 18, 2013, Laricchia.
U.S. Appl. No. 13/920,477, filed Jun. 18, 2013, Laricchia.
U.S. Appl. No. 13/920,507, filed Jun. 18, 2013, Laricchia.
U.S. Appl. No. 13/920,532, filed Jun. 18, 2013, Laricchia.

* cited by examiner

PROCESS FOR TREATING A HYDROCARBON STREAM AND AN APPARATUS RELATING THERETO

FIELD OF THE INVENTION

This invention generally relates to a process for treating a hydrocarbon stream, and an apparatus relating thereto.

DESCRIPTION OF THE RELATED ART

Amine carryover and amine solubility in hydrocarbons, such as fuel gas and liquefied petroleum gas, can cause amine loss and major upsets in caustic extraction and downstream units. When mixed with caustic solutions, amines may cause emulsions in hydrocarbons resulting in off-specification product, high caustic consumption, corrosion of carbon steel in a vapor phase of a separator, and loss of production due to operating at lower hydrocarbon flow rates. It would be desirable to eliminate these problems by making the hydrocarbon streams entering the extraction unit amine free. Often, the amine carryover is accentuated when processing a liquefied petroleum gas derived from fluid catalytic cracking and coker units. Knockout drums can remove entrained amine, and amine water washes may remove soluble amine; however, such devices are typically insufficient to provide the requisite separation. Hence, there is a desire to provide a suitable amine process that can reduce costs by reducing vessel size and possibly eliminate equipment.

SUMMARY OF THE INVENTION

One exemplary embodiment can be a process for treating a hydrocarbon stream. The stream can include passing the hydrocarbon stream into a vessel containing a packed zone and a coalescing zone, passing an amine stream into the vessel at a location above an inlet for the hydrocarbon stream, and withdrawing the hydrocarbon stream.

Another exemplary embodiment may be a process for treating a hydrocarbon stream. The process may include passing the hydrocarbon stream having hydrogen sulfide to an absorption zone, passing an amine stream to an absorption zone for absorbing hydrogen sulfide, and passing the hydrocarbon stream from the absorption zone to a coalescing zone for removing one or more amines.

A further embodiment can be an apparatus for removing hydrogen sulfide from a hydrocarbon stream. The apparatus may include an amine absorption zone having a first vessel containing a packed zone and a coalescing zone, a prewash zone including a second vessel downstream of the amine absorption zone, an extraction zone downstream from the prewash zone, and an alkali regeneration zone in communication with the extraction zone. Often, the coalescing zone has a hydrophilic mesh.

The embodiments disclosed herein can use a coalescing media to enhance the separation of amine and hydrocarbons at the top of an absorber column and/or in a knockout drum. Generally, this coalescing media enhances the separation of spent water and hydrocarbons in the amine water washes. Typically, the coalescing media has hydrophilic properties including a coated or an uncoated mesh, a corrugated sheet media, or other liquid-liquid coalescing media.

One exemplary coalescing media may include a fluoropolymer-coated mesh for separating hydrocarbons from an aqueous solution, although a stainless steel mesh may alternatively be utilized. Preferably, smaller vessels and/or elimination of some vessels may reduce the overall cost and facilitate construction of modular units. Thus, the embodiments disclosed herein may reduce both capital and operating costs of the treating units.

DEFINITIONS

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules. Furthermore, a superscript "+" or "−" may be used with an abbreviated one or more hydrocarbons notation, e.g., $C3^+$ or $C3^-$, which is inclusive of the abbreviated one or more hydrocarbons. As an example, the abbreviation "$C3^+$" means one or more hydrocarbon molecules of three carbon atoms and/or more. In addition, the term "stream" may be applicable to other fluids, such as aqueous and non-aqueous solutions of alkaline or basic compounds, such as sodium hydroxide.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 50%, and preferably about 70%, by mole, of a compound or class of compounds in a stream. If referring to a solute in solution, e.g., one or more disulfide compounds in an alkaline solution, the term "rich" may be referenced to the equilibrium concentration of the solute. As an example, about 5%, by mole, of a solute in a solvent may be considered rich if the concentration of solute at equilibrium is about 10%, by mole.

As used herein, the term "substantially" can mean an amount of at least generally about 80%, preferably about 90%, and optimally about 99%, by mole, of a compound or class of compounds in a stream.

As used herein, the terms "absorbent" and "absorber" include, respectively, an adsorbent and an adsorber, and relates, but is not limited to, absorption, and/or adsorption.

As used herein, the term "coupled" can mean two items, directly or indirectly, joined, fastened, associated, connected, or formed integrally together either by chemical or mechanical means, by processes including stamping, molding, or welding. What is more, two items can be coupled by the use of a third component such as a mechanical fastener, e.g., a screw, a nail, a bolt, a staple, or a rivet; an adhesive; or a solder.

As used herein, the term "coalescer" may be a media containing an optionally coated metal mesh, glass fibers, or other material to facilitate separation of immiscible liquids of similar density.

As used herein, the term "immiscible" can mean two or more phases that cannot be uniformly mixed or blended.

As used herein, the term "phase" may mean a liquid, a gas, or a suspension including a liquid and/or a gas, such as a foam, aerosol, or fog. A phase may include solid particles. Generally, a fluid can include one or more gas, liquid, and/or suspension phases.

As used herein, the term "alkali" can mean any substance that in solution, typically a water solution, has a pH value greater than about 7.0, and exemplary alkali can include sodium hydroxide, potassium hydroxide, or ammonia. Such an alkali in solution may be referred to as "an alkaline solution" or "an alkaline" and includes caustic, i.e., sodium hydroxide in water.

As used herein, the term "parts per million" may be abbreviated herein as "ppm" and "weight ppm" may be abbreviated herein as "wppm".

As used herein, the term "mercaptan" typically means thiol and may be used interchangeably therewith, and can include compounds of the formula RSH as well as salts thereof, such as mercaptides of the formula $RS^-M^+$ where R is a hydrocarbon group, such as an alkyl or aryl group, that is saturated or unsaturated and optionally substituted, and M is a metal, such as sodium or potassium.

As used herein, the term "disulfides" can include dimethyldisulfide, diethyldisulfide, and ethylmethyldisulfide, and possibly other species having the molecular formula RSSR' where R and R' are each, independently, a hydrocarbon group, such as an alkyl or aryl group, that is saturated or unsaturated and optionally substituted. Typically, a disulfide is generated from the oxidation of a mercaptan-containing caustic and forms a separate hydrocarbon phase that is not soluble in the aqueous caustic phase. Generally, the term "disulfides" as used herein excludes carbon disulfide ($CS_2$).

As used herein, the weight percent or ppm of sulfur, e.g., "wppm-sulfur" is the amount of sulfur, and not the amount of the sulfur-containing species unless otherwise indicated. As an example, methylmercaptan, $CH_3SH$, has a molecular weight of 48.1 with 32.06 represented by the sulfur atom, so the molecule is about 66.6%, by weight, sulfur. As a result, the actual sulfur compound concentration can be higher than the wppm-sulfur from the compound. An exception is that the disulfide content in caustic can be reported as the wppm of the disulfide compound.

As used herein, the term "lean" can describe a fluid optionally having been treated and desired levels of sulfur, including one or more mercaptans and one or more disulfides for treating one or more C1-C4 hydrocarbons.

As used herein, the term "regeneration" with respect to a solvent stream can mean removing one or more disulfide sulfur species from the solvent stream to allow its reuse.

As used herein, the terms "degrees Celsius" may be abbreviated "° C." and the term "kilopascal" may be abbreviated "KPa" and all pressures disclosed herein are absolute.

As depicted, process flow lines in the figures can be referred to, interchangeably, as, e.g., lines, pipes, branches, distributors, streams, effluents, feeds, products, portions, catalysts, withdrawals, recycles, suctions, discharges, and caustics.

DETAILED DESCRIPTION

Figure 1:
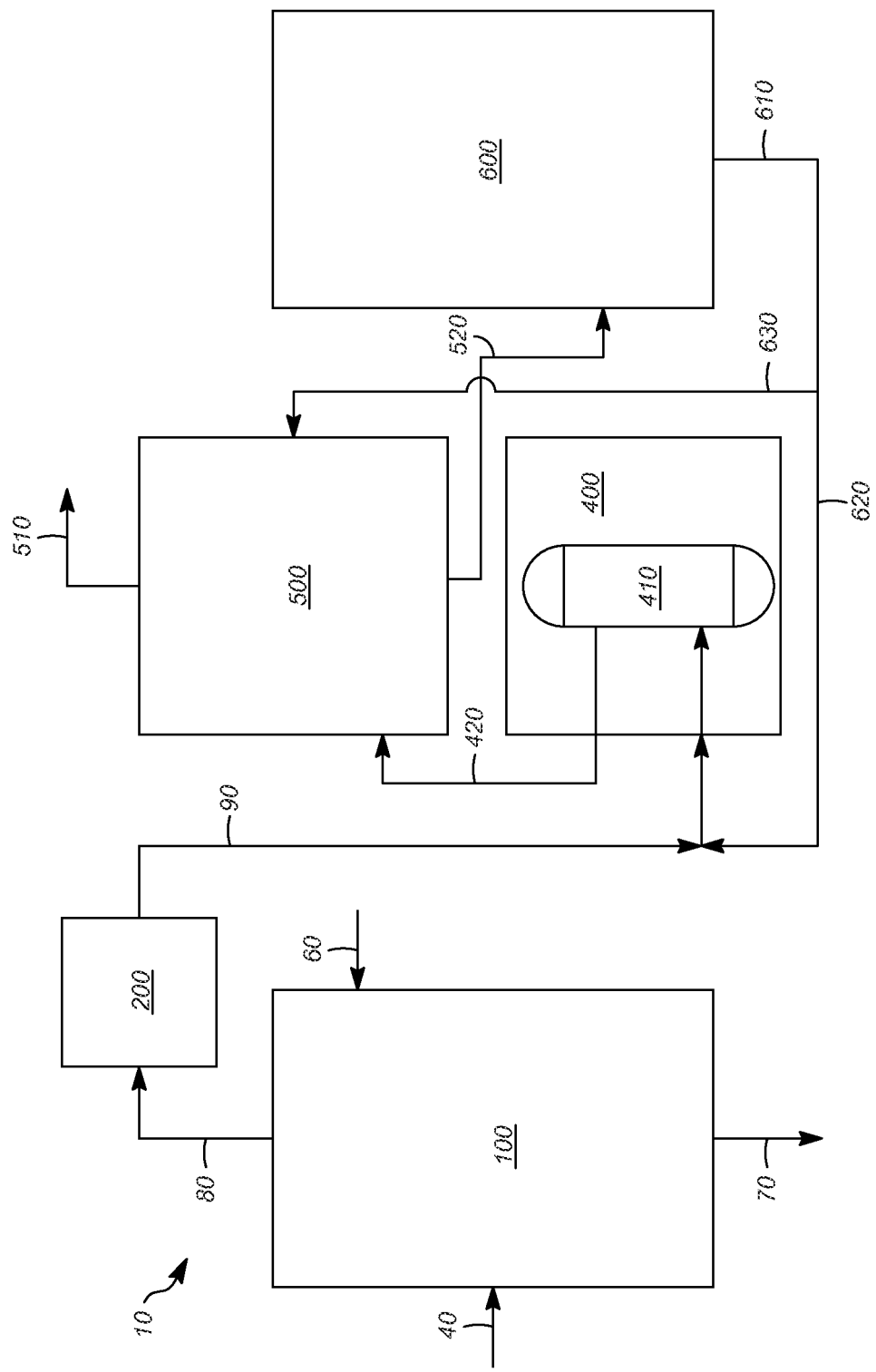
FIG. 1 is a schematic depiction of an exemplary apparatus.

Referring to FIG. 1, an apparatus 10 for removing hydrogen sulfide from a hydrocarbon stream can include an amine absorption zone or absorption zone 100, a coalescing zone 200, a prewash zone 400, an extraction zone 500, and an alkali regeneration zone 600. A hydrocarbon stream 40 including one or more $C4^-$ hydrocarbons, such as a liquefied petroleum gas or a fuel gas containing one or more thiol compounds, may be provided to the amine absorption zone 100. Generally, the hydrocarbon stream 40 may be rich in or substantially has one or more $C4^-$ hydrocarbons. The hydrocarbon stream 40 may be one or more liquids, gases, or a mixture of one or more gases and liquids.

The amine absorption zone 100 can receive an amine stream 60 for absorbing hydrogen sulfide. The amine is described in further detail below. In one exemplary embodiment, the amine absorption zone 100 can include an amine absorber or a first vessel containing a series of trays. The hydrocarbon stream 40 can be provided via a distributor below a mid-point of the vessel. A nozzle for delivering the amines can be disposed toward the top of the vessel to allow counter-current contact of the amines descending in the vessel and the hydrocarbon ascending in the vessel. Generally, the amines in the vessel react with hydrogen sulfide to yield thiol amides.

The conditions within the amine absorption zone 100 can include a temperature of about 0- about 100° C., and pressure of about 100- about 4,000 KPa. Generally, there are about 10- about 25 moles of amine for each mole of combined hydrogen sulfide and carbon dioxide to be removed. Typically, the hydrocarbon stream 40 contains approximately about 1,000- about 2,000 wppm of hydrogen sulfide that is reduced down to about 15 wppm of hydrogen sulfide concentration in the withdrawn hydrocarbon stream. An amine effluent stream rich in thiol amides can exit the bottom of the amine absorber vessel while a hydrocarbon stream 80 may exit the top of the amine absorber vessel with a substantially reduced concentration of hydrogen sulfide. Additionally, carbon dioxide or other acid gases that are possibly present in the hydrocarbon stream 40 may also react with the amines and are absorbed into the amine effluent stream leaving the amine absorber vessel.

A rich amine stream 70 can exit the amine absorption zone 100, which may be regenerated. An exemplary amine absorption zone is disclosed in, e.g., U.S. Pat. No. 7,381,309. Another version of an amine absorption zone 100 is discussed hereinafter.

The hydrocarbon stream 80 from the amine absorption zone 100 can be sent to the optional coalescing zone 200, as hereinafter described. A hydrocarbon stream 90 can be obtained and sent to the prewash zone 400 containing a prewash, or a second vessel 410 for removing hydrogen sulfide by converting to, e.g., sodium sulfide. Subsequently, a prewash effluent 420 can be sent to an extraction zone 500 downstream from the prewash zone 400. A lean alkali stream 610 at least partially obtained from the alkali regeneration zone 600 may be split into a portion 620 combined with the hydrocarbon stream 90 prior to entering the prewash zone 400 and another portion 630 provided to the extraction zone 500. Generally, a product stream 510 is obtained from the extraction zone 500 and a rich alkali stream 520 can be sent to the alkali regeneration zone 600, which may include an oxidation vessel and disulfide separator. The rich alkali stream 520 may be regenerated to provide a lean alkali stream 610 provided to the hydrocarbon stream 90 and extraction zone 500, as discussed above. Exemplary prewash, extraction, and alkali regeneration zones 400, 500, and 600 are disclosed in, e.g., U.S. Pat. No. 7,381,309.

Figure 2:
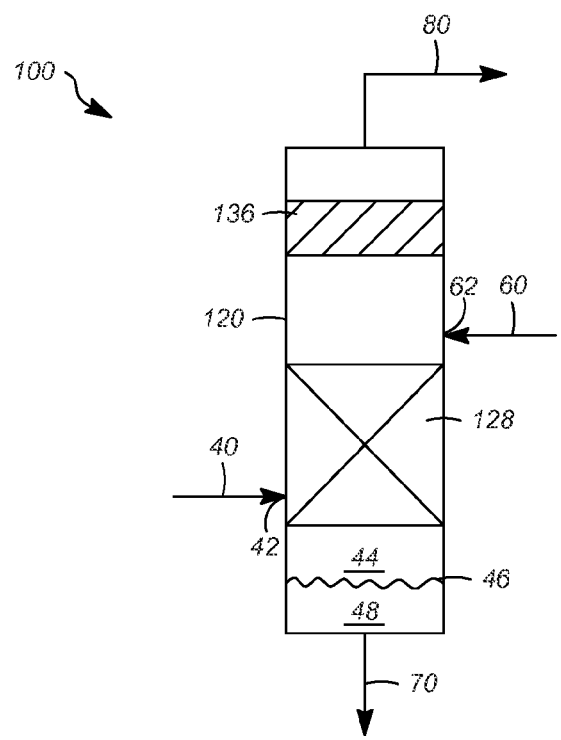
FIG. 2 is an elevational, cross-sectional view of an exemplary absorption zone.

Referring to FIG. 2, an exemplary amine absorption zone or absorption zone 100 is depicted having a vessel or first vessel 120, which can contain a packed zone 128 and a coalescing zone 136. The packed zone 128 may include one or more rings or one or more trays made from ceramic or metal; such as Raschig rings, pall rings, and sieve trays. The packed zone 128 can receive the hydrocarbon stream 40 at an inlet 42 below an inlet 62 for an amine stream 60 provided above the packed zone 128. Usually, the amine stream 60 includes at least one alkanolamine, including at least one of monoethanolamine, diethanolamine, and methyl diethanolamine, preferably monoethanolamine and diethanolamine in a water solution. Often, the amine stream 60 can include about 15- about 40%, preferably about 10- about 20%, by weight, amine with the balance water.

The vessel 120 can contain a hydrocarbon phase 44 and an amine phase 48 forming an interface 46. The amine phase 48 can be withdrawn as the rich amine stream 70 and regenerated. The hydrocarbon phase 44 can rise past the packed zone 128 to the coalescing zone 136, which can include a hydrophilic media. Generally, the hydrophilic media includes at least one of a metal mesh that is optionally coated; one or more glass fibers; or a metal, such as stainless steel, mesh. Desirably, the coating may be an oleophobic and/or hydrophilic coating usually suited for an oil phase. One exemplary mesh may have a coating sold under the trade designation COALEX or KOCH-OTTO YORK™ separations technology by Koch-Glitsch, LP of Wichita, Kans. Alternatively, the coalescing zone 136 can include one or more vanes, such as metal and optionally coated with a hydrophilic coating. As such, the coalescing zone 136 can minimize the formation of emulsions, thereby potentially lowering utility and chemical costs, such as amine, alkali, and process water, and lowering operating costs.

Alternatively, if the hydrocarbons are in a gas phase, such as a fuel gas, the coalescing zone 136 may be replaced with a demister. Such a demister may be a vane or mesh, and constructed from any suitable material such as a metal, e.g., stainless steel. The hydrocarbon phase 44 can rise through the coalescing zone 136 and exit the vessel 120 as the hydrocarbon stream 80, which can pass to the coalescing zone 200 or directly to the prewash zone 400.

Figure 3:
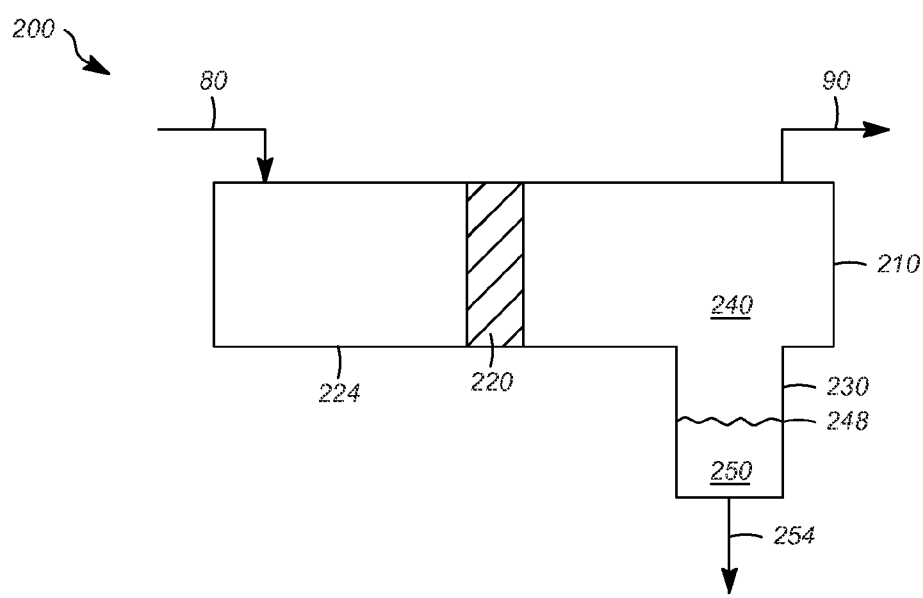
FIG. 3 is an elevational, cross-sectional view of an exemplary coalescing zone.

Referring to FIG. 3, the coalescing zone 200 for removing one or more amines is depicted. The coalescing zone 200 may include a vessel 210, which in this depicted embodiment is orientated horizontally, but in other embodiments may be orientated vertically. Often the vessel 210 includes a body 224 formed integrally with a boot 230. Typically, the vessel 210 contains a coalescing media 220 that occupies a vertical, cross-sectional slice of the body 224 of the vessel 210, thereby dividing the body 224 into two chambers. The hydrocarbon stream 80 can enter the vessel 210 and pass through the coalescing media 220 to form two phases, namely a hydrocarbon phase 240 and an amine phase 250 forming an interface 248 typically in the boot 230. The coalescing media 220 can include at least one of a mesh, optionally coated, and one or more vanes. Desirably, the coalescing media is hydrophilic and can be one of the specific examples as described above. The amine phase 250 can be withdrawn as a rich amine stream 254 and be sent to any suitable destination, including an amine regeneration unit. A control valve can regulate the amount of the rich amine stream 254 for maintaining a desired level in the boot 230 by communicating with a level controller. The hydrocarbon phase 240 can be withdrawn as the hydrocarbon stream 90 and provided to the downstream extraction zone 500.

Figure 4:
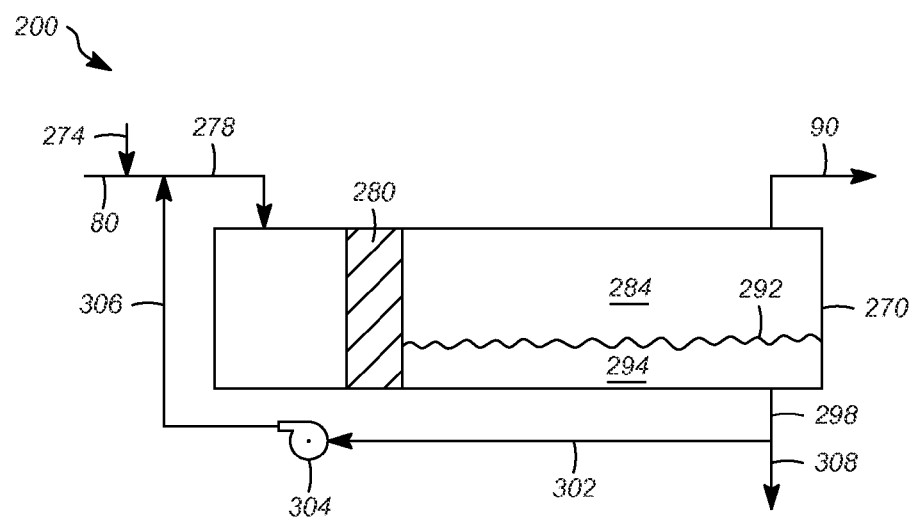
FIG. 4 is an elevational, cross-sectional view of another exemplary coalescing zone.

Referring to FIG. 4, another version of the coalescing zone 200 is depicted. In this exemplary version, the coalescing zone 200 can include a substantially horizontal vessel 270 that may receive the hydrocarbon stream 80 that is combined with a stream 274 including substantially water and a discharge stream 306, as hereinafter described, to form a combined stream 278 that may enter the vessel 270. The vessel 270 can contain a coalescing media 280 that can occupy a substantially vertical slice of the vessel 270 and divide the vessel 270 into two chambers. The coalescing media 280 can separate the combined stream into a hydrocarbon phase 284 forming an interface 292 with an aqueous phase 294. The aqueous phase 294 can be withdrawn as a water stream 298 and split into a recycle stream 302 and a purge stream 308, which can be sent to any suitable destination, including an amine regeneration unit. A control valve can regulate the amount withdrawn as the water stream 298 and communicate with a level controller to maintain the level in the vessel 270. The recycle stream 302 can be provided to a suction of a pump 304 and the discharge stream 306 combined with the streams 80 and 274. The hydrocarbon stream 90 can be withdrawn from the hydrocarbon phase 284 in the vessel 270 and provided to the downstream extraction zone 500.

Figure 5:
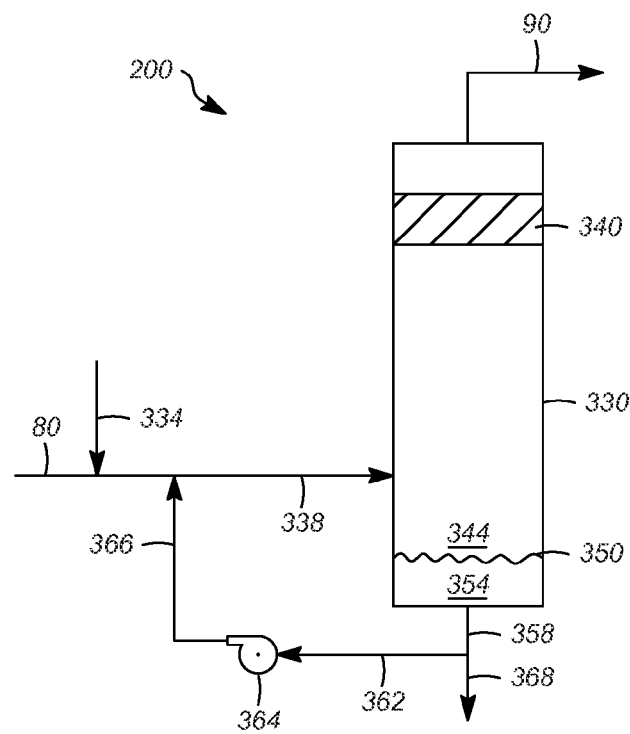
FIG. 5 is an elevational, cross-sectional view of a further exemplary coalescing zone.

Referring to FIG. 5, a further version of the coalescing zone 200 is depicted. In this exemplary version, the coalescing zone 200 can include a substantially vertical vessel 330 that may receive the hydrocarbon stream 80 that is combined with a stream 334 including substantially water and a discharge stream 366, as hereinafter described, to form a combined stream 338 that may enter the vessel 330. The vessel 330 can contain a coalescing media 340 that can occupy a substantially horizontal slice of the vessel 330 and divide the vessel 330 into two chambers. The coalescing media 340 can separate water from the hydrocarbons. The vessel 330 can also contain a hydrocarbon phase 344 forming an interface 350 with an aqueous phase 354. The aqueous phase 354 can be withdrawn as a water stream 358 and split into a recycle stream 362 and a purge stream 368, which can be sent to any suitable destination, including an amine regeneration unit. A control valve can regulate the amount withdrawn as the water stream 358 and communicate with a level controller to maintain the level in the vessel 330. The recycle stream 362 can be provided to a suction of a pump 364 and the discharge steam 366 combined with the streams 80 and 334. The hydrocarbon stream 90 can be withdrawn from the hydrocarbon phase 344 in the vessel 330 and provided to the downstream extraction zone 500.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A process for treating a hydrocarbon stream, comprising:
  A) passing the hydrocarbon stream into a vessel containing a packed zone and a coalescing zone;
  B) passing an amine stream into the vessel at a location above an inlet for the hydrocarbon stream; and
  C) withdrawing the hydrocarbon stream.

2. The process according to claim 1, wherein the packed zone comprises one or more rings or one or more trays.

3. The process according to claim 2, wherein the packed zone comprises one or more rings, which in turn comprises ceramic or metal.

4. The process according to claim 1, wherein the coalescing zone comprises at least one of a mesh and one or more vanes.

5. The process according to claim 1, wherein the coalescing zone comprises a mesh wherein the mesh comprises a coating.

6. The process according to claim 5, wherein the coating comprises a hydrophilic coating.

7. The process according to claim 1, wherein the amine comprises at least one alkanolamine.

8. The process according to claim 7, wherein the alkanolamine comprises at least one of monoethanolamine, diethanolamine, and methyl diethanolamine.

9. The process according to claim 1, wherein the hydrocarbon stream comprises about 500- about 50,000 ppm, by weight, hydrogen sulfide upstream of the vessel.

10. The process according to claim 1, wherein the withdrawn hydrocarbon stream comprises no more than about 15 ppm, by weight, hydrogen sulfide.

11. The process according to claim 9, wherein the hydrocarbon stream further comprises one or more $C_4^-$ hydrocarbons.

12. A process for treating a hydrocarbon stream, comprising:
   A) passing the hydrocarbon stream comprising hydrogen sulfide to an absorption zone;
   B) passing an amine stream to an absorption zone for absorbing hydrogen sulfide; and
   C) passing the hydrocarbon stream from the absorption zone to a coalescing zone for removing one or more amines.

13. The process according to claim 12, wherein the coalescing zone is comprised in a horizontal vessel.

14. The process according to claim 12, wherein the coalescing zone is comprised in a vertical vessel.

15. The process according to claim 13, further comprising passing a water stream to the coalescing zone.

16. The process according to claim 14, further comprising passing a water stream to the coalescing zone.

17. The process according to claim 12, wherein the coalescing zone comprises at least one of a mesh and one or more vanes.

18. The process according to claim 17, wherein the coalescing zone comprises the mesh wherein the mesh comprises a coating.

19. The process according to claim 18, wherein the coating comprises a hydrophilic coating.

* * * * *